(12) United States Patent  
Martinelli et al.

(10) Patent No.: US 7,007,699 B2  
(45) Date of Patent: Mar. 7, 2006

(54) SURGICAL SENSOR

(75) Inventors: Michael A. Martinelli, Winchester, MA (US); Mark W. Hunter, Broomfield, CO (US); Sheri McCoid, Broomfield, CO (US); Paul Kessman, Broomfield, CO (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 63 days.

(21) Appl. No.: 10/289,869

(22) Filed: Nov. 7, 2002

(65) Prior Publication Data

US 2003/0066538 A1    Apr. 10, 2003

Related U.S. Application Data

(63) Continuation of application No. 09/428,721, filed on Oct. 28, 1999, now Pat. No. 6,499,488.

(51) Int. Cl.  
*A61B 19/00* (2006.01)

(52) U.S. Cl. ........................................ 128/899

(58) Field of Classification Search ................ 600/407, 600/424, 508, 486, 561, 427; 128/899; 606/76, 606/69, 72, 73  
See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,294,083 A | 12/1966 | Alderson |
| 3,367,326 A | 2/1968 | Frazier |
| 3,439,256 A | 4/1969 | Kähne et al. |
| 3,577,160 A | 5/1971 | White |
| 3,674,014 A | 7/1972 | Tillander |
| 3,702,935 A | 11/1972 | Carey et al. |
| 3,704,707 A | 12/1972 | Halloran |
| 3,868,565 A | 2/1975 | Kuipers |
| 3,941,127 A | 3/1976 | Froning |
| 4,037,592 A | 7/1977 | Kronner |
| 4,052,620 A | 10/1977 | Brunnett |

(Continued)

FOREIGN PATENT DOCUMENTS

CA            964149           3/1975

(Continued)

OTHER PUBLICATIONS

Laitinen, Lauri V., "Noninvasive multipurpose stereo-adapter," Neurological Research, Jun. 1987, pp. 137-141.

(Continued)

*Primary Examiner*—Max F. Hindenburg  
*Assistant Examiner*—Brian Szmal  
(74) *Attorney, Agent, or Firm*—Harness, Dickey & Pierce, P.L.C.

(57) ABSTRACT

An integrated surgical anchor/localization sensor is disclosed. The anchor is adapted to be secured to an anatomical structure and contains a sensor housing. A receiver is located within the sensor housing and is adapted to sense reference signals generated by a surgical guidance system. A transmitter, connected to the receiver, conveys to a processor signals received by the receiver, so that the signals transmitted by the receiver are indicative of a current position of the anchor. Various other structures and methods are also disclosed.

57 Claims, 4 Drawing Sheets

U.S. PATENT DOCUMENTS

| | | |
|---|---|---|
| 4,054,881 A | 10/1977 | Raab |
| 4,117,337 A | 9/1978 | Staats |
| 4,173,228 A | 11/1979 | Van Steenwyk et al. |
| 4,202,349 A | 5/1980 | Jones |
| 4,262,306 A | 4/1981 | Renner |
| 4,287,809 A | 9/1981 | Egli et al. |
| 4,314,251 A | 2/1982 | Raab |
| 4,317,078 A | 2/1982 | Weed et al. |
| 4,328,813 A | 5/1982 | Ray |
| 4,339,953 A | 7/1982 | Iwasaki |
| 4,358,856 A | 11/1982 | Stivender et al. |
| 4,368,536 A | 1/1983 | Pfeiler |
| 4,396,885 A | 8/1983 | Constant |
| 4,403,321 A | 9/1983 | Kruger |
| 4,418,422 A | 11/1983 | Richter et al. |
| 4,422,041 A | 12/1983 | Lienau |
| 4,431,005 A | 2/1984 | McCormick |
| 4,485,815 A | 12/1984 | Amplatz |
| 4,543,959 A | 10/1985 | Sepponen |
| 4,548,208 A | 10/1985 | Niemi |
| 4,572,198 A | 2/1986 | Codrington |
| 4,584,577 A | 4/1986 | Temple |
| 4,613,866 A | 9/1986 | Blood |
| 4,618,978 A | 10/1986 | Cosman |
| 4,621,628 A | 11/1986 | Brudermann |
| 4,625,718 A | 12/1986 | Olerud et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,673,352 A | 6/1987 | Hansen |
| 4,706,665 A | 11/1987 | Gouda |
| 4,719,419 A | 1/1988 | Dawley |
| 4,722,056 A | 1/1988 | Roberts et al. |
| 4,722,336 A | 2/1988 | Kim et al. |
| 4,727,565 A | 2/1988 | Ericson |
| 4,737,794 A | 4/1988 | Jones |
| 4,737,921 A | 4/1988 | Goldwasser et al. |
| 4,750,487 A | 6/1988 | Zanetti |
| 4,771,787 A | 9/1988 | Wurster et al. |
| 4,791,934 A | 12/1988 | Brunnett |
| 4,793,355 A | 12/1988 | Crum et al. |
| 4,797,907 A | 1/1989 | Anderton |
| 4,803,976 A | 2/1989 | Frigg et al. |
| 4,821,206 A | 4/1989 | Arora |
| 4,821,731 A | 4/1989 | Martinelli et al. |
| 4,836,778 A | 6/1989 | Baumrind et al. |
| 4,845,771 A | 7/1989 | Wislocki et al. |
| 4,849,692 A | 7/1989 | Blood |
| 4,862,893 A | 9/1989 | Martinelli |
| 4,889,526 A | 12/1989 | Rauscher et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,099,845 A | 3/1992 | Besz et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,152,288 A | 10/1992 | Hoenig et al. |
| 5,160,337 A | 11/1992 | Cosman |
| 5,161,536 A | 11/1992 | Vikomerson et al. |
| 5,178,164 A | 1/1993 | Allen |
| 5,178,621 A | 1/1993 | Cook et al. |
| 5,186,174 A | 2/1993 | Schlöndorff et al. |
| 5,187,475 A | 2/1993 | Wagener et al. |
| 5,188,126 A | 2/1993 | Fabian et al. |
| 5,190,059 A | 3/1993 | Fabian et al. |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,228,442 A | 7/1993 | Imran |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,291,199 A | 3/1994 | Overman et al. |
| 5,295,483 A | 3/1994 | Nowacki et al. |
| 5,297,549 A | 3/1994 | Beatty et al. |
| 5,299,254 A | 3/1994 | Dancer et al. |
| 5,299,288 A | 3/1994 | Glassman et al. |
| 5,305,091 A | 4/1994 | Gelbart et al. |
| 5,305,203 A | 4/1994 | Raab |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,333,168 A | 7/1994 | Fernandes et al. |
| 5,353,795 A | 10/1994 | Souza et al. |
| 5,353,800 A * | 10/1994 | Pohndorf et al. ............ 600/486 |
| 5,353,807 A | 10/1994 | DeMarco |
| 5,368,030 A | 11/1994 | Zinreich et al. |
| 5,375,596 A | 12/1994 | Twiss et al. |
| 5,377,678 A | 1/1995 | Dumoulin et al. |

| Patent | Date | Inventor |
|---|---|---|
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,397,329 A | 3/1995 | Allen |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,458,718 A | 10/1995 | Venkitachalam |
| 5,464,446 A | 11/1995 | Dreessen et al. |
| 5,478,341 A | 12/1995 | Cook et al. |
| 5,478,343 A | 12/1995 | Ritter |
| 5,480,422 A | 1/1996 | Ben-Haim |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlöndorff et al. |
| 5,503,416 A | 4/1996 | Aoki et al. |
| 5,513,637 A | 5/1996 | Twiss et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,568,809 A | 10/1996 | Ben-Haim |
| 5,572,999 A | 11/1996 | Funda et al. |
| 5,573,533 A | 11/1996 | Strul |
| 5,575,794 A | 11/1996 | Walus et al. |
| 5,383,454 A | 12/1996 | Bucholz |
| 5,583,909 A | 12/1996 | Hanover |
| 5,588,430 A | 12/1996 | Bova et al. |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A * | 4/1998 | Ben-Haim ............... 600/407 |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,699 A | 6/1998 | Bosnyak et al. |
| 5,769,789 A | 6/1998 | Wang et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,728 A | 9/1998 | Kuhn |
| 5,810,735 A | 9/1998 | Halperin et al. |
| 5,823,192 A | 10/1998 | Kalend et al. |
| 5,823,958 A | 10/1998 | Truppe |
| 5,828,725 A | 10/1998 | Levinson |

| | | |
|---|---|---|
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,884,410 A | 3/1999 | Prinz |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schultz et al. |
| 5,913,820 A | 6/1999 | Bladen et al. |
| 5,920,395 A | 7/1999 | Schultz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,981 A | 9/1999 | Cosman |
| 5,950,629 A | 9/1999 | Taylor et al. |
| 5,951,475 A | 9/1999 | Gueziec et al. |
| 5,954,647 A | 9/1999 | Bova et al. |
| 5,954,796 A | 9/1999 | McCarty et al. |
| 5,967,980 A | 10/1999 | Ferre et al. |
| 5,968,047 A * | 10/1999 | Reed .......................... 606/76 |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,073,043 A | 6/2000 | Schneider |
| 6,104,944 A | 8/2000 | Martinelli |
| 6,118,845 A | 9/2000 | Simon et al. |
| 6,122,538 A | 9/2000 | Sliwa, Jr. et al. |
| 6,131,396 A | 10/2000 | Duerr et al. |
| 6,139,183 A | 10/2000 | Graumann |
| 6,149,592 A | 11/2000 | Yanof et al. |
| 6,156,067 A | 12/2000 | Bryan et al. |
| 6,161,032 A | 12/2000 | Acker |
| 6,167,296 A | 12/2000 | Shahidi |
| 6,172,499 B1 | 1/2001 | Ashe |
| 6,175,756 B1 | 1/2001 | Ferre et al. |
| 6,223,067 B1 | 4/2001 | Vilsmeier |
| 6,233,476 B1 | 5/2001 | Strommer et al. |
| 6,246,231 B1 | 6/2001 | Ashe |
| 6,273,896 B1 | 8/2001 | Franck et al. |
| 6,298,262 B1 | 10/2001 | Franck et al. |
| 6,332,089 B1 | 12/2001 | Acker et al. |
| 6,341,231 B1 | 1/2002 | Ferre et al. |
| 6,351,659 B1 | 2/2002 | Vilsmeier |
| 6,381,485 B1 | 4/2002 | Hunter et al. |
| 6,424,856 B1 | 7/2002 | Vilsmeier et al. |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,470,207 B1 | 10/2002 | Simon et al. |
| 6,474,341 B1 | 11/2002 | Hunter et al. |
| 6,493,573 B1 | 12/2002 | Martinelli et al. |
| 6,498,944 B1 * | 12/2002 | Ben-Haim et al. .......... 600/407 |
| 6,499,488 B1 | 12/2002 | Hunter et al. |
| 6,527,443 B1 | 3/2003 | Vilsmeier et al. |
| 6,551,325 B1 | 4/2003 | Neubauer et al. |
| 6,584,174 B1 | 6/2003 | Schubert et al. |
| 6,609,022 B1 | 8/2003 | Vilsmeier et al. |
| 6,611,700 B1 | 8/2003 | Vilsmeier et al. |
| 6,640,128 B1 | 10/2003 | Vilsmeier et al. |
| 6,694,162 B1 | 2/2004 | Hartlep |
| 6,701,179 B1 | 3/2004 | Martinelli et al. |

FOREIGN PATENT DOCUMENTS

| | | |
|---|---|---|
| DE | 3042343 A1 | 6/1982 |
| DE | 3831278 A1 | 3/1989 |
| DE | 4233978 C1 | 4/1994 |
| DE | 10085137 | 11/2002 |
| EP | 0 319 844 A1 | 1/1988 |
| EP | 0419729 A1 | 9/1989 |
| EP | 0350996 A1 | 1/1990 |
| EP | 0 651 968 A1 | 8/1990 |
| EP | 0 581 704 B1 | 7/1993 |
| EP | 0 655 138 B1 | 8/1993 |
| EP | 0 894 473 A2 | 1/1995 |
| FR | 2417970 | 2/1979 |
| JP | 2765738 | 6/1998 |
| WO | WO 88/09151 | 12/1988 |
| WO | WO 89/05123 | 6/1989 |
| WO | WO 91/03982 | 4/1991 |
| WO | WO 91/04711 | 4/1991 |
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 94/23647 | 10/1994 |
| WO | WO 94/24933 | 11/1994 |
| WO | WO 96/11624 | 4/1996 |
| WO | WO 98/08554 | 3/1998 |
| WO | WO 98/38908 | 9/1998 |
| WO | WO 99/60939 | 12/1999 |
| WO | WO 01/30437 A1 | 5/2001 |

OTHER PUBLICATIONS

Kelly, Patrick J., Kall, Bruce A. et al., "Computer-assisted stereotaxic laser resection of intra-axial brain neoplasms, J. Neurosurg.," vol. 64, Mar. 1986, pp. 427-439.

Laitinen, Lauri V., Liliequist, Bengt, et al., "An Adapter for Computed Tomography-Guided, Stereotaxis," Surg. Neurol., 1985, pp. 559-566.

Horner, Neil and Potts, Gordon D., "A Comparison of CT-Stereotaxic Brain Biopsy Techniques," Investigative Radiology, Sep.-Oct. 1984, pp. 367-373.

Heilbrun, Peter M., Roberts, Theodore S., et al., "Preliminary experience with Brown-Roberts-Wells (BRW) computerized tomography stereotaxic guidance system," J. Neurosurg. vol. 59, Aug. 1983, pp. 217-222.

Leksell, L. and Jernberg, B., "Stereotaxis and Tomography A Technical Note," 1980, Acta Neurochururgica 52, pp. 1-7.

The Laitinen Stereotactic System, E-2—E6.

Bucholz, Richard D., Ho, Hector W., and Rubin, Jason P., "Variables affecting the accuracy of stereotactic localization using computerized tomography," J. Neurosurg., vol. 79, Nov. 1993, pp. 667-673.

Foley, Kevin T., "The StealthStation™: Three Dimensional Image-Interactive Guidance for the Spine Surgeon," Spinal Frontiers, Apr. 1996, pp. 7-9.

Barrick, E. Frederick and Mulhern, Peter J., "Technical Difficulties with the Brooker-Wills Nail in Acute Fractures of the Femur," J. of Orthopaedic Trauma, vol. 4, 1990, pp. 144-150.

Barrick, E. Frederick, "Distal Locking Screw Insertion Using a Cannulated Drill Bit: Technical Note," Journal of Orthopaedic Trauma, vol. 7, 1993, pp. 248-251.

Smith, Kurt R., Frank, Kevin J., and Bucholz, Richard D., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

"Prestige Cervical Disc System Surgical Technique" Brochure, 12 pgs.

Adams et al., "Orientation Aid for Head and Neck Surgeons," Innov. Tech. Biol. Med., vol. 13, No. 4, 1992, pp. 409-424.

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel, Edmund C. et al., "Magnetic Source Imaging: a Review of the Magnes System of Biomagnetic Technologies Incorporated," Neurosurgery, vol. 33, No. 2 (Aug. 1993), pp. 252-259.

Bouazza-Marouf et al.; "Robotic-Assisted Internal Fixation of Femoral Fractures", IMECHE., pp. 51-58 (1995).

Brack, C. et al., "Accurate X-ray Based Navigation in Computer-Assisted Orthopedic Surgery," CAR '98, pp. 716-722.

Bryan, "Bryan Cervical Disc System Single Level Surgical Technique", Spinal Dynamics Brochure, 2002, pp. 1-33 (described by Vincent Bryan).

Bucholz, Richard D. et al., "Variables affecting the accuracy of stereotactic localization using computerized tomography," Journal of Neurosurgery, vol. 79, Nov. 1993, pp. 667-673.

Champleboux et al., "Accurate Calibration of Cameras and Range Imaging Sensors: the NPBS Method," IEEE International Conference on Robotics and Automation, Nice, France, May, 1992.

Champleboux, Guilleme "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Gildenberg et al., "Calculation of Stereotactic Coordinates from the Computed Tomographic Scan," Neurosurgery, vol. 10, No. 5, May 1982, pp. 580-586.

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. '96, pp. 42-51.

Gueziec et al., "Registration of Computed Tomography Data to a Surgical Robot Using Fluoroscopy: A Feasibility Study," Computer Science/Mathematics, Sep. 27, 1996, 6 pages.

Hamadeh et al, "Kinematic Study of Lumbar Spine Using Functional Radiographies and 3D/2D Registration," TIMC UMR 5525—IMAG, 1997.

Hamadeh et al., "Automated 3-Dimensional Computed Tomographic and Fluorscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hatch, et al. "Reference-Display System for the Integration of CT Scanning and the Operating Microscope," Thesis, Thayer School of Engineering, Oct. 1984, pp. 1-189.

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Hounsfield, "Computerized transverse axial scanning (tomography): Part 1. Decription of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique For Accurate Transpedicular Screw Fixation Using CT Data and a 3-D Optical Localizer," TIMC, Faculte de Medecine de Grenoble.

Lavallee et al., "Image guided operating robot: a clinical application in stereotactic neurosurgery," Proceedings of the 1992 IEEE Internation Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 0926-0927.

Lavallee, "VI Adaption de la Methodologie a Quelques Applications Cliniques," Chapitre VI, pp. 133-148.

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Phillips et al., "Image Guided Orthopaedic Surgery Design and Analysis," Trans Inst. MC, vol. 17, No. 5, 1995, pp. 251-264.

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Smith et al., "Computer Methods for Improved Diagnostic Image Display Applied to Stereotactic Neurosurgery," Automedical, vol. 14, 1992, pp. 371-382.

Viant et al., "A Computer Assisted Orthopaedic System for Distal Locking of Intramedullary Nails," Proc. of MediMEC '95, Bristol, 1995, pp. 86-91.

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Weese et al., "An Approach to 2D/3D Registration of a Vertebra in 2D X-ray Fluoroscopies with 3D CT Images," pp. 119-128.

Germano, "Instrumentation, Technique, and Technology", Neurosurgery, vol. 37, No. 2, Aug. 1995, pp. 348-350.

Merloz, et al., "Computer Assisted Spine Surgery", Clinical Assisted Spine Surgery, No. 337, pp. 86-96.

Hatch, et al., "Reference-Display System for the Integration of CT Scanning and the Operating Microscope", Proceedings of the Eleventh Annual Northeast Bioengineering Conference, May, 1985, pp. 252-254.

* cited by examiner

SURGICAL SENSOR

This application is a continuation of U.S. patent application Ser. No. 09/428,721, filed Oct. 28, 1999, now U.S. Pat. No. 6,499,488, the contents of which are incorporated herein by reference in their entirety, and from which priority is claimed.

BACKGROUND OF THE INVENTION

1. Field of the Invention

The present invention relates to a surgical sensor which may be integrated with an anatomical anchor. The sensor has particular applicability in surgical procedures where it is desirable to track the relative movement of one or more structures.

2. Description of the Related Art

Many surgical procedures are planned and guided using images obtained from imaging systems such as magnetic resonance imagers (MRIs), computer tomographic imagers (CTs), x-ray imagers, positron emission tomographic (PET) scanners, and photo-emission computer technology (SPECT). These systems permit physicians to obtain detailed preoperative (or intraoperative) views of anatomical structures using noninvasive procedures. Once these images are obtained, the physician typically uses the images to plan a corrective surgical procedure. With the patient lying on an operating table, the images may be "registered" with the corresponding physical space of the patient, and displayed on a screen in the operating room (OR). As the physician navigates probes or other medical instruments within the patient, sensors on the instruments relay positional information to a computer. The computer, in turn, overlays a display of the position of the instrument on the image of the anatomical structure. In this way, the physician may navigate through a surgical procedure by viewing a display screen in the OR. An example of a related art system is found in U.S. patent application Ser. No. 08/809,904, now U.S. Pat. No. 6,236,875, entitled "Surgical Navigation System including Reference and Localization Frame," and which is fully incorporated herein by reference.

Until now, the tracking of anatomical structures has been largely limited to external tracking, either by taping a sensor to a patient's skin, or by affixing an external clamp to the patient, such as a Mayfield clamp, attached externally to a patient's head.

U.S. patent application Ser. No. 08/931,654, now U.S. Pat. No. 6,347,240, entitled "Bone Navigation System" which is incorporated fully herein by reference discloses a system which employs screws extending from a bone fragment through a patient's skin and connected to a platform external to the patient. Tracking elements such as, for example, emitters are located on the platform so that when a bone fragment moves, so too does the platform with the connected tracking elements. An array in the OR tracks movement of the tracking elements, and this movement is correlated to the movement of the bone fragment, in order to precisely track the movement of the bone fragment. Alternatively, clamps may be used, in place of screws, to secure an array of tracking elements to a bone structure. While such related art systems may generally be reliable, their structure is somewhat cumbersome, especially when the movement of multiple anatomical structures needs to be tracked. In addition, the use of the tracking elements and receiving array requires an unobstructed line of sight therebetween which not only limits implantation within a patient, but also can lead to interference.

For these reasons, in procedures such as those involving the spine or the reconstruction or repair of vertebral bodies, fractured skulls, fragmented bones, or other damaged boney structures, it has been somewhat difficult to track the relative movement of multiple anatomical structures.

SUMMARY OF THE INVENTION

It is an object of certain aspects of this invention to enable the detection of anatomical structure movement during medical procedures without the use of cumbersome external equipment fixed to the patient.

It is another object of certain aspects of the invention to provide a localization system for internal and/or external anatomical structures that do not require an unobstructed line of sight between a positional sensor and a detector.

It is a further object of certain aspects of this invention to provide a localization system for internal anatomical structures which may be employed with minimal invasive procedures.

It is another object of certain aspects of this invention to provide an integrated anchor and localization sensor that may be deployed with relative ease.

It is yet another object of certain aspects of this invention to provide an anatomical anchor which may serve as both a preprocedural and intraprocedural fiducial marker.

It is an additional object of certain aspects of this invention to provide a reliable localization marker which may be placed in a patient in advance of a procedure and which may remain in the patient for a period of time following the procedure.

It is a further object of certain aspects of the present invention to enable movement detection, with five or six degrees of freedom, of an anatomical structure or surgical instrument (whether the instrument be an anchor, a catheter, or any other medical instrument).

These and other objects of the invention may be inherent or derived from the detailed description of the preferred embodiments.

The invention, in its broadest sense, may comprise one or more of the following aspects, either alone or in combination with one or more additional elements:

an anatomical anchor/sensor,
a receiver on an anchor for sensing signals generated external to the anchor,
a transmitter on an anchor for conveying signals indicative of the anchor's location,
a signal generator on an anchor,
a connection for securing a receiver to an anatomical anchor,
a receiver and/or transmitter on a surgical screw, staple, pin rod, needle or soft tissue anchor,
an electromagnetic sensing coil on an anchor,
a magnet on an anchor,
an electromagnetic sensor having multiple collinear coils wound at differing angles, whether disposed on an anchor, a catheter, or other medical instrument,
hard-wiring a transmitter on an anchor to a processor,
affixing a wireless transmitter to an anchor,
affixing a conductive electrode to an anatomical anchor,
a surgical screw having a hollow containing a sensor,
affixing a sensor to anchor using potting material,
a sensor housing for the head of a screw,
an attachable/detachable sensor mount for an anchor,
a grasping region for permitting medical personnel to screw a portion of a screw/sensor into an anatomical structure, an integrated anatomical anchor/sensor where the sensor is detachable, methods and apparatuses for deploying an integrated anchor/sensor, methods for making and using the above items, procedures where the relative movement of instruments and/or anatomical structures are tracked and displayed, and any other novel and unobvious aspects of the following disclosure and/or claims.

DETAILED DESCRIPTION OF THE PREFERRED EMBODIMENTS

Figure 1A:
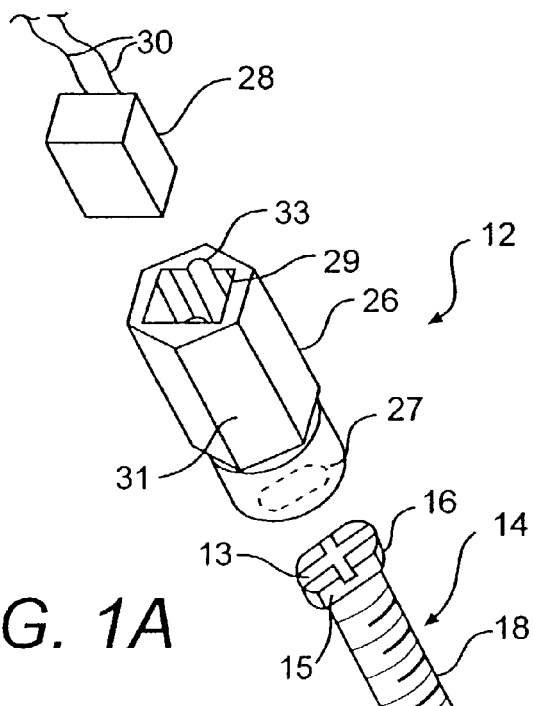
FIG. 1A is an exploded view of an integrated sensor and bone screw in accordance with one embodiment of the present invention.

The invention will now be described in connection with the Figures wherein like parts are numbered with the same reference numerals for ease of discussion.

In accordance with the invention, there is provided an integrated surgical anchor/localization sensor. An example of such an integrated unit is designated by reference number 12 in FIG. 1.

According to the invention, the anchor is configured to be secured to an anatomical structure. As illustrated in FIG. 1, an anchor in accordance with the invention may, by way of example, include a surgical screw 14. Screw 14 has a head portion 16, and a threaded portion 18. The threaded portion 18 is configured to be secured into boney structure such as portions of long bones, vertebral bodies, the skull, or any other boney anatomical structure. In an preferred embodiment, the anchor may be a 2.2 mm cross-drive screw, 3–7 mm in length. Preferably, the screw has keyed head portions 15 so that a connector may be securely fastened to it. Screw 15 may also contain slots 13 enabling the screw to be driven by various convention surgical screw drivers. It is also preferable for the screw 14 to be constructed of a material that will appear on an image scan and that will not cause interference with the surgical guidance system in which it is intended to be used. If an anchor is scanably detectable, it may alternatively be used as a fiducial marker. By way of example, when used with electromagnetic guidance systems, the screw may be constructed of aluminum.

While aspects of the invention are described herein in connection with surgical screws the invention in its broadest sense is not so limited. Other anchors may be used in connection with the invention. By way of example only, such other anchors may include surgical staples, pins, rods, soft tissue anchors such as pigtails, and headframe (e.g., Mayfield) pins.

Figure 2A:
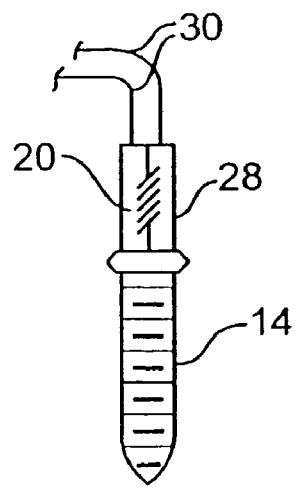
FIG. 2A is a schematic diagram of a single coil sensor in accordance with the invention.
Figure 2B:
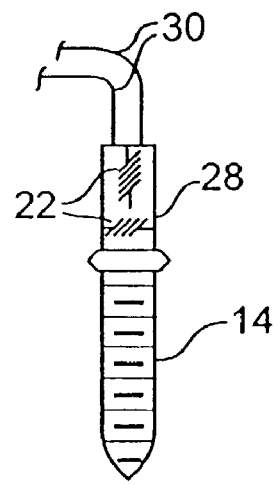
FIG. 2B is a schematic diagram of a dual-orthogonal coil sensor in accordance with the invention.
Figure 2C:
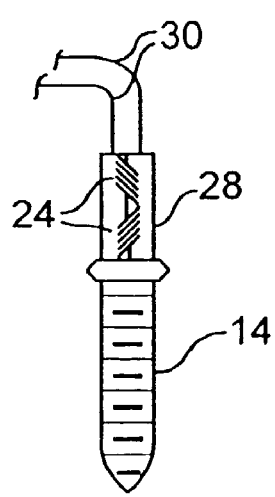
FIG. 2C is a schematic diagram of a dual-coaxial coil sensor in accordance with the invention.
Figure 3:
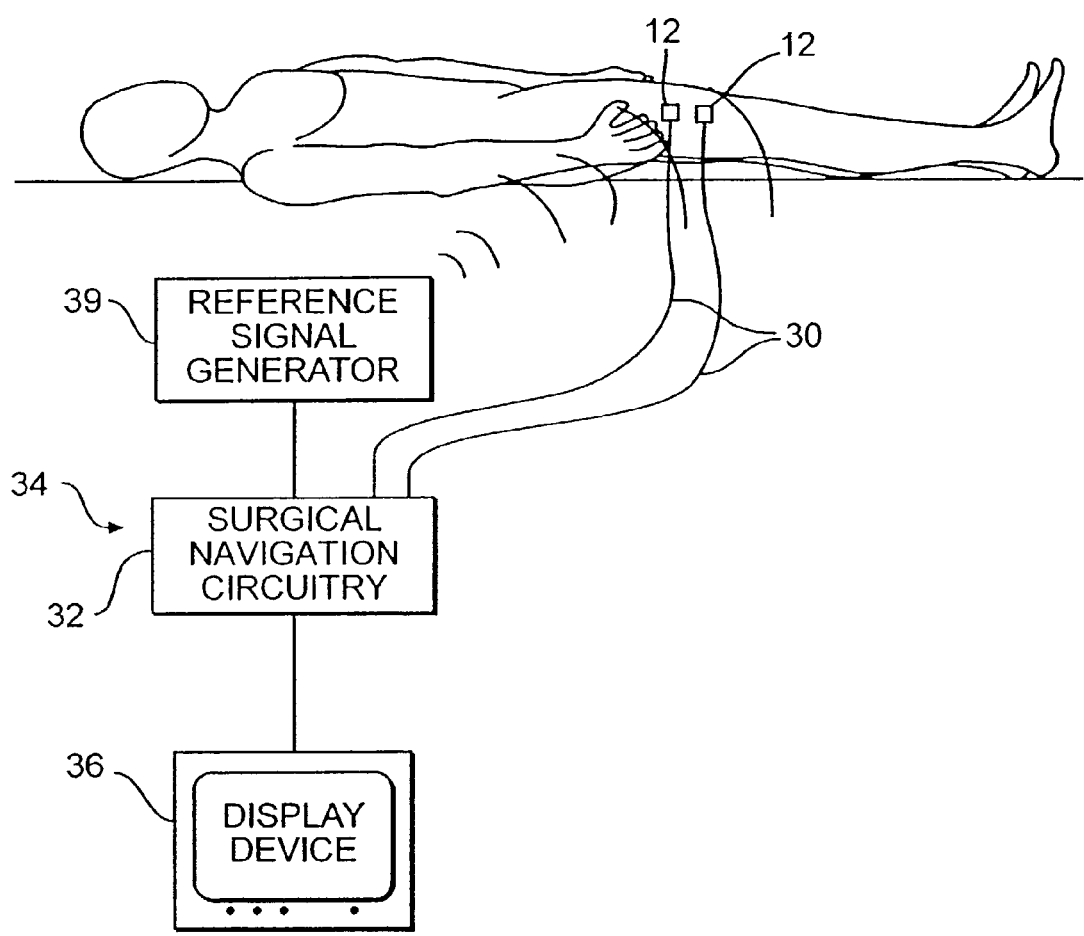
FIG. 3 is a schematic diagram of a preferred system of the invention and the environment of its use.

In accordance with the invention, there is also provided a receiver for sensing reference signals generated by a surgical guidance system. Such a system typically includes a reference signal generator 39 as schematically depicted in FIG. 3. When an electromagnetic guidance system is to be used in connection with the invention, the receiver may include at least one electromagnetic sensor 28 as schematically depicted in FIGS. 2A–2C. The invention is not limited to any specific localization guidance system or algorithm. Nevertheless, an example of an acceptable system and algorithm may be found in U.S. Pat. No. 5,592,939, entitled: "Method and System for Navigating a Catheter Probe," and which is fully incorporated herein by reference.

FIG. 2A illustrates a sensor 28 having a single coil 20. Depending on the specifics of the guidance system employed, such a sensor is typically capable of detecting position with either three or five degrees of freedom. In contrast, FIGS. 2B and 2C illustrate sensors 28 having multiple coils capable of detecting position with up to six degrees of freedom. More particularly, the coil arrangement illustrated in FIG. 2B enables a reference signal to be detected with two orthogonal sensing coils 22. Alternatively, a plurality of collinear coils may be employed. For example, in the coaxial arrangement illustrated in FIG. 2C, two collinear sensing coils 24 are wound at differing or opposing angles. While any opposing angles will work, a preferred angle is 90°. In this manner, each coil will provide unique feedback in response to the same reference signal generated by an electromagnetic guidance system.

The coil arrangement of FIG. 2C also has applicability in connection with medical devices other than anchors. For example, the collinear nature of the arrangement makes it particularly suitable for devices that have working channels such as catheters where coils of differing angles may be wrapped around the working channel to thereby minimize the size of the device.

The coil(s) of sensor 28 may be constructed of 40 AWG wire wrapped approximately 200 turns. Alternatively, the sensors may be 10 $\mu$H–1000 $\mu$H surface-mounted inductors, preferably non-shielded. In an alternative embodiment, a conductive localization system may be employed. In this situation, sensor 28 may include a conductive electrode receiver. While the preferred electromagnetic system is disclosed as including coil sensor, any electromagnetic sensor may be used including, but not limited to flux gates and reed switches.

The invention may also include a transmitter for conveying to a processor signals received by the receiver. In a preferred embodiment, the transmitter may simply include two wires 30 for hardwiring the sensor 28 to the electronics 32 of a surgical guidance system 34 (schematically illustrated in FIG. 3). The transmitter wires 30 may have, at their distal ends (not shown) connectors for selectively connecting them to the surgical guidance system 34. Preferably, the transmitter wires 30 include two pair of 40 AWG twisted bifilar wire, with an outside diameter less than about 0.062 inches. It is also preferable that the transmitter wires be compatible with sterilization processes so that they may be safely used within an anatomical body.

In an alternative embodiment, the transmitter may be wireless, transmitting signals to the surgical guidance system via radio frequency, for example. In such an embodiment, a transmitting circuit and antenna may also be part of sensor 28. Since the details of wireless transmitter systems are known in the art, for brevity, they are not repeated herein. Sensor 28 may further include a battery (not shown) for powering the transmitter. Alternatively, a voltage may be provided to the transmitter by induction using an external coil included as part of sensor 28. Examples of such systems are described in concurrently filed U.S. patent application Ser. No. 09/428,722, now U.S. Pat. No. 6,474,341, entitled "Surgical Communication and Power System" which is fully incorporated herein by reference.

As previously described, a sensor located on an anchor may receive signals from a signal generator external to the patient. The invention may, however, be embodied in a system with the reverse arrangement—i.e., element 28 being a signal generator internal to the patient and the sensor being located external to the patient. In this scenario, and if the invention uses an electromagnetic guidance system, the internal signal generator may, in its simplest form, be a magnet.

Also in accordance with the invention there may be provided a connector for securing the receiver to the anchor, the connector being configured so that the signals conveyed by the transmitter are indicative of a current position of the anchor. As embodied herein, and as illustrated in FIG. 1A, the connector may include housing 26 mounted to the head 16 of screw 14. Housing 26 may include wire relief groove 33 for transmitter wires 30. Housing 26 may also include a keyed opening 27 for receiving corresponding keyed screw head 16. This keyed arrangement prevents housing 26 from rotating on screw 14, thereby ensuring that the sensor 28 remains in a fixed position to provide an accurate reading of the position (i.e., location and/or orientation) of screw 14. Housing 26 preferably has a plurality of flat grasping surfaces 31 enabling the screw to be driven into a boney structure by manipulating the housing 26. Housing 26 may be either detachable, fixedly secured to, or integrally formed with screw 14, so long as it satisfies the function of securing a sensor to the screw. To this end, housing 26 may contain an opening 29 opposite keyed opening 27, for receiving sensor 28. If housing 26 is integrally formed with screw 14, slots 13 may be eliminated or alternatively located at the surface of opening 29.

Figure 1B:
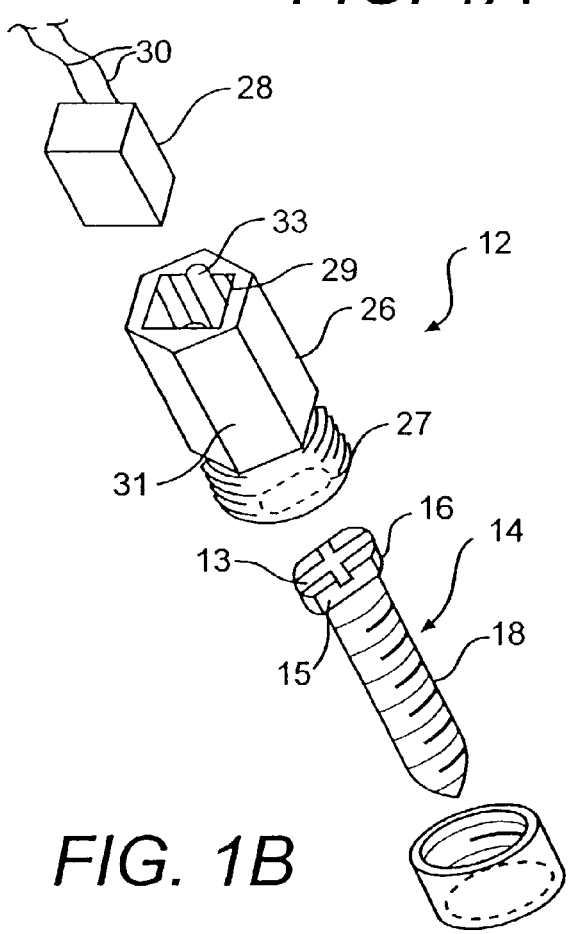
FIG. 1B is an exploded view of an integrated sensor and bone screw in accordance with another embodiment of the present invention.

FIG. 1B illustrates an arrangement similar to FIG. 1A, except that a threaded cap 17 screws onto threaded end 19 of housing 26, securing head 16 of screw 14 to housing 26. With this arrangement, sensor housing 26 may be selectively removed from screw 14.

Sensor 28 may be secured to housing 26 in any appropriate manner. For example, it may snap fit and/or be glued into opening 29. Alternatively, coils or other sensors may be deposited in opening 29 and the opening thereafter filled with a suitable potting material, such as surgical cement. In its broadest sense, the connector of the invention may be any material or mechanism capable of joining the receiver to the anchor, ranging form a quantity of potting material to structures which are molded, mechanically attached to, bonded to, or integrally formed with the anchor.

In an alternative embodiment (not shown) screw 14 may have a partially hollowed construction in lieu of the housing 26, and the receiver may be contained within the hollow. In such an embodiment, the connector may be potting material for securing the receiver within the hollow or may include a cartridge for removably securing the sensor in the hollow. In fact, removability of the sensor from the anchor may be beneficially incorporated into mechanical linkages to provide the physician with flexibility to attached and detach the sensor as the physician sees fit.

Figures 4A, 4B:
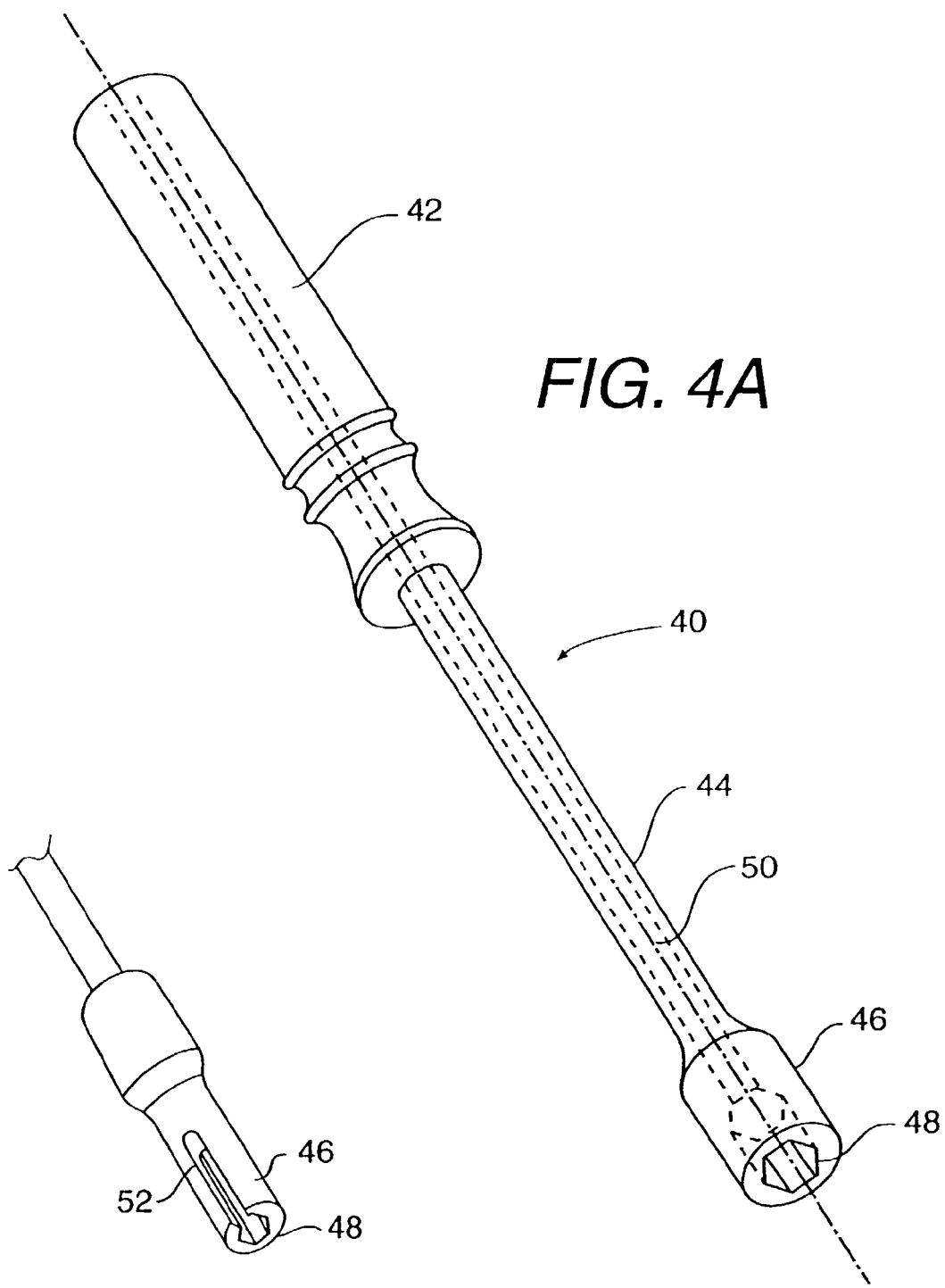
FIG. 4A is a perspective view of an embodiment of a driver associated with deploying the integrated sensors of FIGS. 1A and 1B.
FIG. 4B is a perspective of another embodiment of a driver associated with deploying the integrated sensors of FIGS. 1A and 1B.

While the anchor/sensor of the invention may be used as a fiducial marker, it has particular advantage for use in tracking boney anatomical structures such as vertebral bodies during spinal procedures or bone fragments during reconstructive procedures. By way of example, a physician may obtain an image of a fractured long bone using fluoroscopy or any other imaging device. Using a device such as cannulated driver 40 (illustrated in FIGS. 4A and 4B), the physician may implant screw/sensor into a boney structure. Specifically, driver 40 includes handle 42, neck 44, and socket 46. Socket 46 includes opening 48 shaped to engage grasping surfaces 31 of integrated screw/sensor 12. Driver 40 may include a cannula or opening 50 extending therethrough to accommodate transmitting wires 30. Alternatively, in lieu of opening 50, a slot 52 (FIG. 4B) in an edge of socket 46 may be provided to permit wires 30 to pass therethrough. In use, the physician loads a screw/sensor 12 into socket 48, and passes the loaded socket through an incision adjacent boney structure in which the screw is to be secured. Using handle 42, the physician turns the screw, securing it to the boney structure. Thereafter, the physician removes the driver 40, pulling it over the transmitting wires extended through opening 50 (FIG. 4A) or pulling the slot 52 (FIG. 46) away from wires 30.

After screwing an anchor/sensor 12 into each of the bone fragments, the sensors are then registered with the image, such as in a known manner. With the scanned image appearing on a display device 36, the physician may manipulate the fractured bone fragments, tracking their movement in real-time. This is achievable because the surgical navigation circuitry 32, receiving signals from anchor/sensors 12 in each fractured bone segment, can alter the image appearing on display 36 to reflect a current position of the bone segments. For example, the scanned image may be digitized and correlated to sensors 28 so that as the fractured portions of a bone are moved, simulated movement of those portions occur on display 36. In this way, a physician may precisely reset a fracture bone. Related procedures are disclosed in pending patent application Ser. No. 08/809,404, now U.S. Pat. No. 6,236,875, entitled "Surgical Navigation System Including Reference Frame and Localization Frame", and Ser. No. 08/931,654, now U.S. Pat. No. 6,347,240, entitled "Bone Navigation System", both of which are fully incorporated herein by reference.

It will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. A method of detecting and tracking a current position of a tissue or bone anchor, comprising:

sensing, via a receiver associated with the tissue or bone anchor, reference signals generated by a surgical navigation system;

conveying, via a transmitter associated with the receiver, positional signals as a function of a current location of (i) the receiver and (ii) the reference signals generated by the surgical navigation system;

wherein the receiver is configured so that the positional signals correspond to the current position of the tissue or bone anchor.

2. A method according to claim 1, further including sensing the reference signals generated by the surgical navigation system with at least one electromagnetic coil.

3. A method according to claim 1, further including sensing the reference signals generated by the surgical navigation system with two or more electromagnetic coils arranged coaxially and wound at different angles.

4. A method according to claim 1, further including conveying the positional signals to a surgical localization system via one or more wires.

5. A method according to claim 1, further including conveying the positional signals to a surgical localization system via a wireless link.

6. The method according to claim 1, further including sensing the reference signals generated by the surgical navigation system with a plurality of electromagnetic coils arranged collinearly.

7. The method according to claim 1, further including sensing the reference signals generated by the surgical navigation system with a plurality of electromagnetic coils arranged orthogonally.

8. A system for attaching a surgical anchor/localization sensor to a bone in a patient for use during a medical procedure, said system comprising:
   a bone anchor operable to be substantially rigidly secured to the bone of the patient;
   a localization sensor to identify a current position of said bone anchor;
   a connector securing and retaining said localization sensor to said bone anchor to form an integrated bone anchor/localization sensor; and
   a device engage and drive at least a portion of said integrated bone anchor/localization sensor into the bone of the patient.

9. The system as defined in claim 8 wherein the bone is a bone selected from a group comprising a vertebral body, a skull, a fragmented bone, a long bone, and any combination thereof.

10. The system as defined in claim 8 wherein said system is formed as a head clamp.

11. The system as defined in claim 8 wherein said system is formed as a head frame pin.

12. The system as defined in claim 8 wherein said bone anchor is selected from a group comprising a surgical screw, a surgical staple, a surgical pin, a surgical rod, a needle, and any combination thereof.

13. The system as defined in claim 8 wherein said localization sensor is an electromagnetic localization sensor.

14. The system as defined in claim 13 wherein said electromagnetic localization sensor is operable to receive electromagnetic signals to identify the current position of said bone anchor.

15. The system as defined in claim 13 wherein said electromagnetic localization sensor transmits electromagnetic signals to identify the current position of said bone anchor.

16. The system as defined in claim 13 wherein said electromagnetic localization sensor includes a plurality of collinear coils wound at differing angles.

17. The system as defined in claim 13 wherein said electromagnetic localization sensor includes a plurality of electromagnetic coils coaxially arranged and wound at differing angles.

18. The system as defined in claim 13 wherein said electromagnetic localization sensor includes at least two orthogonal sensing coils.

19. The system as defined in claim 13 wherein said electromagnetic sensor is selected from a group comprising a flux gate, a reed switch, a coil, a magnet, and any combination thereof.

20. The system as defined in claim 8 wherein said localization sensor is a conductive localization sensor.

21. The system as defined in claim 8 wherein said localization sensor includes a receiver operable to sense reference signals generated by a surgical guidance system and a transmitter operable to transmit positional signals indicative of the current position of said bone anchor.

22. The system as defined in claim 8 wherein said localization sensor is a wireless localization sensor.

23. The system as defined in claim 22 wherein said wireless localization sensor includes a battery.

24. The system as defined in claim 22 wherein said wireless localization sensor employs induction to power said wireless localization sensor.

25. The system as defined in claim 21 wherein said transmitter includes a wire for hardwiring said localization sensor to a surgical localization system.

26. The system as defined in claim 8 wherein said device is a driver having a proximal handle, an intermediate neck, and a distal engaging end.

27. The system as defined in claim 26 wherein said distal engaging end is a socket operable to engage said bone anchor/localization sensor.

28. The system as defined in claim 26 wherein said distal engaging end is a blade of a screwdriver operable to engage said bone anchor/localization sensor.

29. The system as defined in claim 26 wherein said driver is a cannulated driver defining a cannula extending through said driver.

30. The system as defined in claim 29 wherein said cannula is operable to enable the driver to be positioned over a wire extending from said localization sensor.

31. The system as defined in claim 27 wherein said driver defines a slot in an edge of said socket operable to enable wires to pass therethrough.

32. The system as defined in claim 27 wherein said anchor/localization sensor includes a socket engaging surface operable to be engaged by said socket of said driver.

33. The system as defined in claim 28 wherein said anchor/localization sensor includes a blade engaging surface operable to be engaged by said blade of said driver.

34. The system as defined in claim 8 wherein said connector is integrally formed with said bone anchor.

35. The system as defined in claim 8 wherein said connector is detachably secured to said bone anchor.

36. The system as defined in claim 8 wherein said connector includes a housing defining an opening operable to receive said localization sensor.

37. The system as defined in claim 36 wherein said housing defines a wire relief groove operable to receive a wire.

38. The system as defined in claim 36 wherein said localization sensor is selectively detachable from said housing.

39. A method of attaching and tracking a location of a surgical anchor/localization sensor attached to a bony structure of a patient, said method comprising:
   imaging the bony structure to generate an image of the bony structure;
   providing an anchor having a localization sensor attached thereto;
   driving the anchor into the bony structure to secure the anchor and the localization sensor to the bony structure;

registering the localization sensor to the image of the bony structure; and tracking the movement and location of the bony structure with the localization sensor.

40. The method as defined in claim 39 further comprising detachably removing the localization sensor from the anchor.

41. The method as defined in claim 39 wherein driving the anchor into the bony structure further includes screwing the anchor into the bony structure by way of a threaded anchor.

42. The method as defined in claim 39 further comprising passing wires from the localization sensor through a cannulated driver and driving the anchor into the bony structure.

43. The method as defined in claim 39 further comprising passing wires from the localization sensor into a slot of a driver and driving the anchor into the bony structure.

44. The method as defined in claim 39 further comprising engaging the surgical anchor/localization sensor with a socket of a driver to drive the anchor into the bony structure.

45. The method as defined in claim 39 further comprising detaching a housing affixed to the anchor to move the localization sensor.

46. The method as defined in claim 39 further comprising driving the anchor into a bony structure selected from a group comprising vertebral body, a skull, a fragmented bone, a long bone, and any combination thereof.

47. The method of claim 39, wherein said localization sensor includes positioning a plurality of coils substantially coaxially.

48. The method of claim 39, wherein said localization sensor includes positioning a plurality of coils substantially collinearly.

49. The method of claim 39, wherein said localization sensor includes positioning a plurality of coils substantially orthogonally.

50. A system for attaching a surgical anchor/localization sensor to a patient for use during a medical procedure, said system comprising:

an anchor to be substantially secured to the patient;

a localization sensor to identify a current position of said anchor, a connector securing and retaining said localization sensor to said anchor to form an integrated anchor/localization sensor; and a device to engage said integrated anchor/localization sensor and drive at least a portion of said anchor/localization sensor into the patient.

51. The system of claim 50, wherein said localization sensor includes a plurality of coils positioned substantially coaxially.

52. The system of claim 50, wherein said localization sensor includes a plurality of coils positioned substantially collinearly.

53. The system of claim 50, wherein said localization sensor includes a plurality of coils positioned substantially orthogonally.

54. A method of attaching and tracking a location of a surgical anchor/localization sensor attached to a patient, said method comprising:

imaging the patient to generate an image of the patient;

providing an anchor having a localization sensor attached thereto to form an integrated anchor/localization sensor;

driving at least a portion of the integrated anchor/localization sensor into the patient to secure the anchor and the localization sensor to the patient;

registering the localization sensor to the image of the patient; and tracking the movement and location of the patient with the localization sensor.

55. The method of claim 54, wherein providing said localization sensor includes providing a plurality of coils substantially coaxially.

56. The method of claim 54, wherein providing said localization sensor includes providing a plurality of coils substantially collinearly.

57. The method of claim 54, wherein providing said localization sensor includes providing a plurality of coils substantially orthogonally.

* * * * *